United States Patent [19]

Floyd, Jr. et al.

[11] Patent Number: 4,474,810

[45] Date of Patent: Oct. 2, 1984

[54] ARYLGLYOXALS AND THEIR PHARMACEUTICAL USE

[75] Inventors: Middleton B. Floyd, Jr., Suffern, N.Y.; Vern G. DeVries, Ridgewood, N.J.

[73] Assignee: American Cyanamid Company, Stamford, Conn.

[21] Appl. No.: 461,337

[22] Filed: Jan. 27, 1983

[51] Int. Cl.³ ............... A61K 31/185; A61K 143/40
[52] U.S. Cl. ................................ 424/315; 260/511; 568/335; 568/336; 424/331; 546/235

[58] Field of Search ............... 260/511; 568/335, 336; 424/315, 331

[56] References Cited

U.S. PATENT DOCUMENTS 3,408,368  10/1968  Pomot .................. 260/511
3,657,286  4/1972  Micheli ................ 260/511

Primary Examiner—Robert T. Bond
Attorney, Agent, or Firm—Edward A. Conroy, Jr.

[57] ABSTRACT

Arylglyoxals which are new compounds, active as hypoglycemic agents.

14 Claims, No Drawings

ARYLGLYOXALS AND THEIR PHARMACEUTICAL USE

BACKGROUND OF THE INVENTION

This invention relates to arylglyoxals and to hydrates and sodium bisulfite adducts formed from them, which are new compounds useful as pharmaceutical agents. The novel compounds of this invention are hypoglycemic agents capable of ameliorating diabetes mellitus in mammals by acting to simulate and/or potentiate the action of insulin. This invention further relates to methods for treating diabetes mellitus in mammals in need of such treatment. In addition, this invention is concerned with pharmaceutical compositions for the utilization of these compounds in the treatment of diabetes mellitus. Further, this invention relates to the chemical synthesis of the compounds disclosed herein.

The disease diabetes mellitus is characterized by metabolic defects in the production and utilization of glucose which result in the failure to maintain appropriate blood sugar levels. Research on the treatment of diabetes has centered on attempts to normalize fasting and postprandial blood glucose levels. Treatments have included parenteral administration of exogenous insulin, oral administration of drugs, and dietary therapies.

Initially it was thought that hyperglycemia was simply the result of a deficiency in the supply of insulin, the principle hormone which controls glucose metabolism. As a result, research focused on the source of insulin production, the beta cells of the pancreas, and pharmaceutical agents were discovered which stimulated the production of insulin by the pancreas. Although it remains true that a deficiency of insulin does cause hyperglycemia it has now been recognized that other metabolic defects can be a major cause of elevated blood glucose.

In Type I diabetes, also called juvenile onset or insulin-dependent diabetes, insulin deficiency is indeed the cause of hyperglycemia. However, the majority of diabetics suffer from a form of the disease referred to as Type II diabetes, also called maturity onset or noninsulin dependent diabetes. A main characteristic displayed by Type II diabetics is insulin resistance or insulin insensitivity. Insulin resistance is a condition in which available insulin, secreted by the pancreas and circulating in the blood stream, fails to stimulate sufficient glucose uptake and utilization in insulin-sensitive tissue. This inability of certain tissues including liver, muscle, and fat, whose metabolic machinery is normally sensitive to insulin, to utilize glucose efficiently or to control endogenous glucose synthesis and glycogenolysis, results in elevated blood glucose.

Compounds which stimulate and/or potentiate the biological action of insulin would be beneficial in the treatment of hypoglycemia resulting from mild to moderate insulin insufficiency or insulin insensitivity. A compound which would simulate or mimic insulin's action would correct both insulin deficiency and insulin resistance by its own insulin-like action. Further, a compound which would potentiate insulin's action would ameliorate insulin deficiency by rendering the small amount of insulin which is present more efficacious and would decrease insulin resistance directly by acting synergistically to make insulin more effective. Thus compounds which show insulin-like and/or insulin potentiating activity would be beneficial for the treatment of hyperglycemia occuring either in Type I or Type II diabetes.

The compounds of the present invention simulate and potentiate the biological action of insulin. They simulate insulin's action at least in part by promoting the cellular uptake and metabolism of glucose in the absence of insulin. They potentiate insulin's action by exerting a synergistic effect on insulin action in the presence of sub-maximal concentrations of insulin. The exact mechanism by which the compounds of this invention act to produce these effects is not known and the invention should not be construed as limited to any particular mechanism of action. Nonetheless, the compounds of this invention are useful for the treatment of hyperglycemia and diabetes in mammals.

SUMMARY OF THE INVENTION

This invention relates to new arylglyoxals and their addition products, their use in the treatment of diabetes mellitus, pharmaceutical compositions containing them and their chemical synthesis. More particularly, it is concerned with phenylglyoxals of formulae (I), (II), and derivatives of these phenylglyoxals of formulae (III) and (IV), the hydrates and sodium bisulfite adducts of the compounds of formulae (I) and (II).

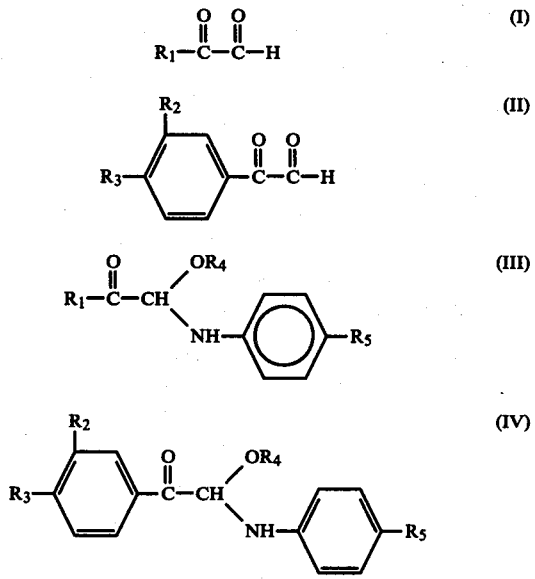

In the above general formulae, $R_1$ is 3-methyl-4-chlorophenyl, 3-chloro-4-methylphenyl, 2-chloro-5-methylphenyl, 2,4-dichlorophenyl or 3,5-dichlorophenyl; $R_2$ is hydrogen, phenoxy, 3,4-dichlorophenoxy or 3,5-dichlorophenoxy; $R_3$ is hydrogen, nitro, 1-piperidino, 1-naphthyloxy, 4-chloro-1-naphthyloxy or 4-chloro-2-naphthyloxy, $R_4$ is hydrogen or ($C_1$-$C_4$)alkyl; and $R_5$ is hydrogen, carboxy, or carboethoxy.

This invention is further concerned with a method of treating diabetes mellitus and/or hyperglycemia in a mammal with compounds of the above formulae, pharmaceutical compositions of matter containing these compounds, and processes for the chemical synthesis of these compounds.

DETAILED DESCRIPTION OF THE INVENTION

Certain of the compounds of this invention may be prepared according to the following reaction sequence:

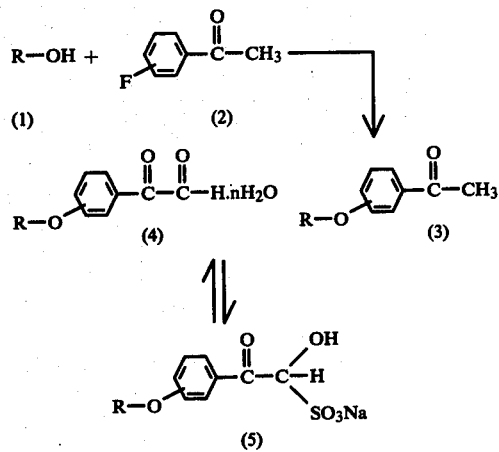

wherein R is phenyl, 3,4-dichlorophenyl, 3,5-dichlorophenyl, 1-naphthyl, 4-chloro-1-naphthyl or 4-chloro-2-naphthyl. In accordance with the above reaction sequence, an appropriately substituted phenol (1) is combined with a fluoroacetophenone (2) and treated with potassium carbonate in dimethylacetamide under an inert atmosphere at reflux for 8–48 hours, then cooled, poured into ice and extracted with ether. The extract is evaporated and distilled, giving the acetophenone (3). The acetophenone (3) is then dissolved in dimethylsulfoxide and treated with aqueous hydrobromic acid at 45°–65° C. for 18–48 hours, poured into ice and extracted with ethyl acetate. The extract, which contains (4) wherein n may vary from almost zero to one or more, is concentrated, dissolved in a mixture of ethanol and water at 5°–70° C. and treated with sodium metabisulfite at the boiling point for 5 minutes, then cooled under argon at 0° C., giving (5). The sodium bisulfite derivatives (5) is then suspended in water at 40°–60° C., acidified, heated at 90°–100° C. for 1–2 hours, cooled and extracted with ether. The ether extract is concentrated giving (4). Compounds of structure (4) are obtained in varying degrees of hydration; that is, n may vary from almost zero to one or more.

Alternatively, as set forth in the following reaction sequence wherein R' is as defined for $R_1$, p-nitrophenyl or p-(1-piperidino)phenyl; the acetophenone (6) is treated with selenium dioxide in aqueous dioxane at reflux, under an inert atmosphere for 12–24 hours. The reaction mixture is then filtered and the filtrate evaporated, giving (7), wherein n may vary from almost zero to one or more, which may be converted to the sodium bisulfite derivative (8) by treatment with sodium metabisulfite in aqueous ethanol.

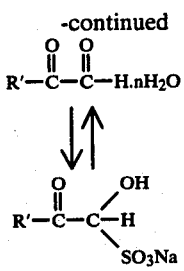

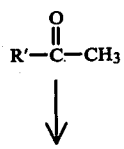

The compounds of this invention were tested for their insulin-like and insulin-potentiating activity according to the following procedure. Male, Wistar strain, Royal Hart rats weighing 125–170 g. were sacrificed by decapitation. Their abdominal cavities were opened and distal or thin portions of epididymal fat pads excised, accumulated, and placed in 0.9% saline. THe tissue was weighed and placed at a density of about 0.4 g/ml. in Krebs-Henseleit bicarbonate (KHB) buffer containing 5 mg. of crude bacterial collagenase per ml. [The KHB is composed of 118 mM sodium chloride; 4.7 mM potassium chloride; 1.2mM calcium chloride; 1.2 mM potassium dihydrogen phosphate; 1.2 mM magnesium sulfate heptahydrate; 25 mM sodium bicarbonate and 0.3 mM glucose and is saturated with oxygen:carbon dioxide (95.5).] The tissues were incubated with collagenase for one hour at 37° C. with gentle agitation in a Dubnoff metabolic shaker. At the end of this digestion period the cells were washed five times with twice their volume of KHB buffer containing fatty acid free bovine serum albumin (Pentex Fraction V) at a concentration of 3%. The digest was filtered through two layers of gauze and suspended in KHB buffer with albumin to a volume ten times the initial total weight of the fat pads. Incubation of one ml. aliquots of the cell suspension was carried out in 17×100 mm plastic Falcon tubes. Cells were incubated in the presence of absence of test compound and insulin. All tubes contained 0.15 $\mu$Ci D-glucose-U-$^{14}$C (specific activity <200 mC/mmole).

Recrystallized porcine insulin (specific activity=25.5 U/mg) was dissolved in 0.9% saline adjusted to pH 3 with hydrochloric acid. The insulin was added to the cells at a concentration of approximately 5 $\mu$U/ml and control or basal cells received comparable volumes of pH 3 saline. Test compounds were dissolved in 50% dimethylsulfoxide-50% ethanol and added to the cells at a concentration of 100 $\mu$g/ml. Control cells received comparable volumes of dimethyl sulfoxide-ethanol.

After the tubes were loaded with insulin and test compound, or other vehicles, and cell suspension, they were capped with sleeve stoppers fitted with hanging, plastic center wells. Each well contained a small section of folded filter paper. The tubes were then gassed for about one minute with oxygen:carbon dioxide (95.5) via needles inserted through the septum of the stopper. Immediately after gassing, the radioactive glucose was injected into the incubate and the tubes were placed in a 37° C. metabolic shaking water bath and were incubated for one hour with agitation.

At the end of the incubation, 0.4 ml. of Hyamine hydroxide and then 0.5 ml. of 5N sulfuric acid were carefully injected into the center well and cell suspension, respectively. The acidified cell suspension was then incubated an additional 30 minutes at room temperature with gentle agitation. At the end of this carbon dioxide collection period, the center wells were dropped into vials containing 10 ml. of Dimiscint ® scintillation cocktail and the radioactivity counted by liquid scintillation spectrometry.

The measurement of carbon dioxide radioactivity in counts per minute produced by these cells in the absence of both test compound and insulin is the basal level (b). Radioactivity produced in the presence of test compounds only, insulin only and both test compound and insulin are (c), (i) and (ci), respectively. Each of (c), (i) and (ci) is then expressed as a percent of the basal value: $C=c/b$; $I=i/b$; $CI=ci/b$. Finally, insulin-like activity (%C/I) is calculated using the formula $$\% C/I = \frac{(100)(C - 100)}{(I - 100)};$$

and insulin-potentiating activity (%P) is calculated using the formula $$\% P = \frac{(100)(CI - C - I + 100)}{(I - 100)}.$$

The results of this test on representative compounds of this invention appear in Table I.

TABLE I

| Compound | % C/I | % P |
|---|---|---|
| [p-(4-chloro-1-naphthyloxy)benzoyl]hydroxy-methanesulfonic acid, sodium salt | 90 | 156 |
| (4-chloro-3-methylbenzoyl)hydroxy-methane-sulfonic acid, sodium salt | 643 | 477 |
| 4-chloro-3-methyl-α-oxo-benzeneacetaldehyde hydrate | 1468 | 405 |
| (2,4-dichlorobenzoyl)hydroxy-methanesulfonic acid, sodium salt | 134 | 223 |
| (6-chloro-3-methylbenzoyl)hydroxy-methanesulfonic acid, sodium salt | 316 | 202 |
| 4'-chloro-2,2-dihydroxy-3'-methylacetophenone | 1467 | 404 |
| 3'-5'-dichloro-2,2-dihydroxy-acetophenone | 390 | 70 |
| α-hydroxy-β-oxo-3-phenoxy-benzeneethanesulfonic acid, sodium salt | 152 | 70 |
| 4-(4-chloro-2-naphthyloxy)-α-oxo-benzene-acetaldehyde, hemihydrate | 311 | 286 |
| 3-(3,5-dichlorophenoxy)-α-hydroxy-β-oxo-benzeneethanesulfonic acid, sodium salt | 122 | 152 |
| 3-(3,4-dichlorophenoxy)-α-hydroxy-β-oxo-benzeneethanesulfonic acid, sodium salt | 129 | 154 |
| 4-[[2-[4-(4-chloro-1-naphthyloxy)phenyl]-1-ethoxy-2-oxoethyl]amino]-benzoic acid | 250 | 305 |
| α-hydroxy-4-(1-naphthyloxy)-β-oxo-benzene-ethanesulfonic acid, sodium salt | 114 | 150 |
| 2,2-dihydroxy-1-[4-(1-naphthyloxy)phenyl]-ethanone | 481 | 96 |
| 4-nitro-α-oxo-benzeneacetaldehyde hemi-hydrate | 583 | 52 |
| 2,2-dihydroxy-1-[4-(1-piperidinyl)phenyl]-ethanone | 391 | 25 |
| 4-[[1-ethoxy-2-(3-phenoxyphenyl)-2-oxoethyl]-amino]-benzoic acid | 75 | 161 |
| 3-chloro-α-hydroxy-4-methyl-β-oxo-benzene ethanesulfonic acid, sodium salt | 517 | 217 |
| 3-chloro-4-methyl-α-oxo-benzeneacetaldehyde hydrate | 935 | 178 |

When the compounds are employed for the above utility, they may be combined with one or more pharmaceutically acceptable carriers, e.g., solvents, diluents and and the like, and may be administered orally in such forms as tablets, capsules, dispersible powders, granules, or suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 5 milligrams to about 100 milligrams per kilogram of animal body weight, preferably given in divided doses two to four times a day, or in sustained release form. For most large mammals, the total daily dosage is from about 500 milligrams to about 5,000 milligrams preferably from about 350 milligrams to 3,500 milligrams. Dosage forms suitable for internal use comprise from about 25 to 500 milligrams of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

4'-(4-Chloro-1-naphthyloxy)acetophenone

A mixture of 42.86 g of 4-chloro-1-naphthol, 27.6 g of p-fluoroacetophenone, 33.12 g of potassium carbonate and 200 ml of dimethylacetamide was heated at 150° C., under argon for 18 hours, then poured into ice water, stirred and extracted with ethyl acetate. The extract was washed with 0.5N sodium hydroxide, 0.5N hydrochloric acid, water and brine, dried and evaporated to a residue. This residue was boiled in hexane, then cooled and the intermediate collected to yield the product as white crystals, mp 95°–99° C.

The other acetophenone starting materials used in the following examples were either commercially available or made essentially by the procedure of Example 1, using other starting materials.

EXAMPLE 2

(4-Chloro-3-methylbenzoyl)hydroxy-methanesulfonic acid, sodium salt

A mixture of 16.8 g. of 4-chloro-3-methylacetophenone, 11.0 g. of selenium dioxide, 4 ml. of water and 120 ml. of dioxane was refluxed overnight, filtered through a pad of diatomaceous earth and concentrated. A 175 ml. portion of ethanol was added and the mixture was filtered through diatomaceous earth. A 9.4 g. portion of sodium bisulfite in 150 ml. of water was added and the mixture was stirred overnight. The solid was collected giving the desired product as a white powder, m.p. 195°–215° C. (dec.).

EXAMPLE 3

4'-Chloro-2,2-dihydroxy-3'-methyl-acetophenone

A 3.0 g. portion of 4-(chloro-3-methylbenzoyl)hydroxy-methanesulfonic acid, sodium salt was heated with 0.5N hydrochloric acid for about one hour, then cooled and the solid recovered, giving the desired product as white crystals, m.p. 84°–94° C. (dec.).

Following the procedures of Examples 1, 2 and 3 and using the indicated starting materials, the products of Examples 4–9, given in Table II, were prepared.

TABLE II

| Example | Starting Material | Product | Physical Constant |
|---|---|---|---|
| 4 | 2',4'-dichloroacetophenone | (2,4-dichlorobenzoyl)hydroxy-methane-sulfonic acid, sodium salt | White Solid |
| 5 | 6-chloro-3-methylacetophenone | (6-chloro-3-methylbenzoyl)hydroxy-methanesulfonic acid, sodium salt | Solid |
| 6 | 3',5'-dichloroacetophenone | 3',5'-dichloro-2,2-dihydroxy-acetophenone | mp 75–76° C. |
| 7 | 1-[4-(1-naphthyloxy)-phenyl]ethanone | α-hydroxy-4-(1-naphthyloxy)-β-oxo-benzeneethanesulfonic acid, sodium salt | Beige Solid |
| 8 | 4'-(4-chloro-1-naphthyloxy)acetophenone | [p-(4-chloro-1-naphthyloxy)benzoyl]-hydroxy-methanesulfonic acid, sodium salt | mp 160–180° C. (dec.) |
| 9 | [p-(4-chloro-1-naphthyloxy)benzoyl]hydroxymethanesulfonic acid, sodium salt | 4-(4-chloro-2-naphthyloxy)-α-oxo-benzeneacetaldehyde, hemihydrate | mp 113–119° C. |

EXAMPLE 10

2,2-Dihydroxy-1-[4-(1-naphthyloxy)phenyl]ethanone

A mixture of 2.62 g. of 1-[4-(1-naphthyloxy)phenyl]ethanone, 4.54 ml of 48% hydrobromic acid and 20 ml of dimethylsulfoxide was heated at 55° C. overnight and then poured into ice water and extracted with ethyl acetate. The extract was washed with water and brine, dried and evaporated to a foam. This foam was purified by chromatography and the resulting oil crystallized from cold methylene chloride, giving the desired product as a white solid, mp 93°–96° C.

Following the procedure of Example 10 and using the indicated starting materials and with the additional step of conversion to the methanesulfonic acid, sodium salt by treatment with aqueous sodium bisulfite where appropriate, the products of Examples 11–13, given in Table III, were derived.

TABLE III

| Example | Starting Material | Product | Physical Constant |
|---|---|---|---|
| 11 | 4-nitroacetophenone | 4-nitro-α-oxo-benzeneacetaldehyde, hemihydrate | mp 55–70° C. (dec.) |
| 12 | 4-(1-piperidinyl)acetophenone | 2,2-dihydroxy-1-[4-(1-piperidinyl)-phenyl]ethanone | mp 100–108° C. |
| 13 | 3'-chloro-4'-methylacetophenone | 3-chloro-α-hydroxy-4-methyl-β-oxo-benzeneethanesulfonic acid, sodium salt | mp 200–220° C. (dec.) |

EXAMPLE 14

3-(3,5-Dichlorophenoxy)-α-hydroxy-β-oxo-benzene ethanesulfonic acid, sodium salt To a stirred solution of 9.3 g of methyl methylthio methylsulfoxide in 60 ml of tetrahydrofuran, in an ice bath under argon, was added a solution of 31.2 ml of 2.4M n-butyllithium in hexane, dropwise via a syringe, maintaining the temperature at 10°–15° C. The solution was stirred 15 minutes, then a solution of 16.02 g of m-(3,5-dichlorophenoxy)benzaldehyde in 30 ml of tetrahydrofuran was added, maintaining the temperature at 0°–10° C. The ice bath was removed, the mixture was stirred for one hour and the tetrahydrofuran evaporated, giving a foam. This foam was dissolved in 120 ml of dimethylsulfoxide and cooled in ice while adding 34.2 ml of 48% hydrobromic acid. The reaction was gradually heated to 50° C. overnight, then poured into cold water and extracted with ethyl acetate. The extract was washed with water, saturated sodium bicarbonate and brine, dried and evaporated. The solid residue was combined with 3.8 g of sodium bisulfite, 50 ml of water and 150 ml of ethanol, refluxed under argon for one hour, then stirred overnight. The solid was collected, giving the desired product as a white solid.

Reaction of the indicated starting materials in the procedure of Example 14 produced the products of Examples 15 and 16, given in Table IV.

TABLE IV

| Example | Starting Material | Product | Physical Constant |
|---|---|---|---|
| 15 | m-(3,4-dichlorophenoxy)-benzaldehyde | 3-(3,4-dichlorophenoxy)-α-hydroxy-β-oxo-benzeneethanesulfonic acid, sodium salt | Cream Solid |
| 16 | m-(phenoxy)benzaldehyde | α-hydroxy-β-oxo-3-phenoxybenzeneethanesulfonic acid, sodium salt | mp 165–180° C. (dec.) |

EXAMPLE 17

4-[[1-Ethoxy-2-(3-phenoxyphenyl)-2-oxoethyl]amino]benzoic acid

A 3.96 g. portion of m-(phenoxy)benzaldehyde was converted to 2,2-dihydroxy-1-[(3-phenoxy)phenyl]ethanone by the procedure of Example 14 (omitting the sodium bisulfite conversion).

A 5.1 g. portion of 2,2-dihydroxy-1-(3-phenoxy)phenyl]ethanone and 2.74 g. of p-aminobenzoic acid in 40 ml. of toluene was refluxed under argon for one hour, then cooled and evaporated to dryness. The residue was added to 40 ml. of ethanol and refluxed for 30 minutes, then cooled to 0° C., giving the desired product, m.p. 117°–127° C. (dec.).

EXAMPLE 18

4-[[2-[4-[(4-Chloro-1-naphthyl)oxy]phenyl]-1-ethoxy-2-oxoethyl]amino]benzoic acid A mixture of 4.2 g. of 2,2-dihydroxy-4-(4-chloro-1-naphthyloxy)-α-oxo-benzeneacetaldehyde hemihydrate, 1.76 g. of p-aminobenzoic acid and 30 ml. of absolute ethanal was refluxed overnight under argon. The solid was collected, boiled in ethanol, cooled and filtered, giving the desired product as a pale yellow solid, m.p. 155°–165° C.

We claim:

1. A compound selected from the group consisting of those of the formula:

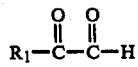

wherein $R_1$ is 3-methyl-4-chlorophenyl, 3-chloro-4-methylphenyl, 2-chloro-5-methylphenyl, 2,4-dichlorophenyl or 3,5-dichlorophenyl and the hydrates and sodium bisulfite adducts thereof.

2. The compound according to claim 1; (4-chloro-3-methylbenzoyl)hydroxy-methanesulfonic acid, sodium salt.

3. The compound according to claim 1; (2,4-dichlorobenzoyl)hydroxy-methanesulfonic acid, sodium salt.

4. The compound according to claim 1; (6-chloro-3-methylbenzoyl)hydroxy-methanesulfonic acid, sodium salt.

5. The compound according to claim 1; 4'-chloro-2,2-dihydroxy-3'-methylacetophenone.

6. The compound according to claim 1; 3',5'-dichloro-2,2-dihydroxy-acetophenone.

7. The compound according to claim 1; 3-chloro-α-hydroxy-4-methyl-β-oxo-benzeneethanesulfonic acid, sodium salt.

8. The compound according to claim 1; 4-chloro-3-methyl-α-oxo-benzeneacetaldehyde hydrate.

9. The compound according to claim 1; 3-chloro-4-methyl-α-oxo-benzeneacetaldehyde hydrate.

10. A method of treating diabetes mellitus in a mammal in need of such treatment which comprises administering to said mammal an effective amount of a compound as recited in claim 1.

11. A method of treating hyperglycemia in a mammal in need of such treatment which comprises administering to said mammal an effective amount of a compound as recited in claim 1.

12. A pharmaceutical composition which comprises an effective antidiabetic amount of a compound as recited in claim 1 in association with a pharmaceutically acceptable carrier.

13. A pharmaceutical composition which comprises an effective hypoglycemic amount of a compound as recited in claim 1 in association with a pharmaceutically acceptable carrier.

14. A process for preparing a compound as recited in claim 1 which comprises reacting an acetophenone with an oxidizing agent selected from the group consisting of hydrobromic acid in dimethylsulfoxide and selenium dioxide and, if necessary, treating the product with sodium bisulfite.

* * * * *